(12) United States Patent
Gagnon et al.

(10) Patent No.: US 8,558,181 B2
(45) Date of Patent: Oct. 15, 2013

(54) POSITRON EMISSION TOMOGRAPHY SYSTEM WITH HYBRID DETECTION GEOMETRIES AND SAMPLING

(75) Inventors: Daniel Gagnon, Twinsburg, OH (US); Wenli Wang, Briarcliff Manor, NY (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 225 days.

(21) Appl. No.: 12/915,705

(22) Filed: Oct. 29, 2010

(65) Prior Publication Data

US 2012/0104263 A1 May 3, 2012

(51) Int. Cl.
*G01T 1/164* (2006.01)
*G21K 1/02* (2006.01)

(52) U.S. Cl.
USPC .................................. 250/363.03; 250/363.1

(58) Field of Classification Search
USPC ..................... 250/363.03, 363.04, 336.1, 366, 250/370.09, 370.11, 370.08, 370.1
See application file for complete search history.

(56) References Cited

U.S. PATENT DOCUMENTS

| 5,210,420 A * | 5/1993 | Hartz et al. ............... 250/363.03 |
| 6,130,430 A * | 10/2000 | DiFilippo ................. 250/363.03 |
| 2007/0090300 A1 * | 4/2007 | Sibomana et al. ........ 250/370.09 |

FOREIGN PATENT DOCUMENTS

JP 2007-041007 2/2007

OTHER PUBLICATIONS

Taiga Yamaya et al., "Influence of TOF Information in OpenPET Image Reconstruction," IEEE Nuclear Science Symposium Conference Record, pp. 2651-2653, (2009).
Dale L. Bailey et al., "ECAT ART—a Continuously Rotating PET Camera: Performance Characteristics, Initial Clinical Studies, and Installation Considerations in a Nuclear Medicine Department," 24 European Journal of Nuclear Medicine 1, pp. 6-15, (Jan. 1997).

* cited by examiner

*Primary Examiner* — David Porta
*Assistant Examiner* — Faye Boosalis
(74) *Attorney, Agent, or Firm* — Oblon, Spivak, McClelland, Maier & Neustadt, L.L.P.

(57) ABSTRACT

A gamma ray detection system includes a plurality of detector modules having a same length, where each detector module is configured to detect gamma rays generated from positron annihilation events. A first detector module of the plurality of detector modules is shifted by a predetermined distance in an axial direction from a second detector module of the plurality of detector modules that is adjacent to the first detector module, where the predetermined distance is less than the length of the detector modules.

17 Claims, 7 Drawing Sheets

POSITRON EMISSION TOMOGRAPHY SYSTEM WITH HYBRID DETECTION GEOMETRIES AND SAMPLING

FIELD

Embodiments described herein relate generally to sampling in a Positron Emission Tomography (PET) detector. Specifically, embodiments described herein relate to an improved method and apparatus to facilitate hybrid sampling in a PET detector.

BACKGROUND

PET Imaging, or positron emitter tomography, starts with the administration (e.g., ingestion or inhalation) of a radiopharmaceutical into a patient, and, in time, the physical and bio-molecular properties of the agent concentrates at specific locations in the human body. The actual spatial distribution, the intensity of the point or region of accumulation, and the kinetics of the process from administration to capture to eventually elimination are all elements that may have a clinical significance. During this whole process, the positron emitter attached to the pharmaceutical agent will emit positrons according to the physical properties of the isotope (i.e., half-life, branching ratio, etc. . . . ). Each emitted positron will eventually interact with an electron of the object to get annihilated and produce two gamma rays at 511 keV at substantially 180 degree apart.

By detecting these two gamma rays, and drawing a line between their locations or line-of-response, the likely location of the original disintegration can be retrieved. While this process only identifies a line of possible interaction, by accumulating a large number of these lines, and through a tomographic reconstruction process, the original distribution can be estimated. In addition to the location of the two scintillation events, if accurate timing (i.e., few hundred picoseconds) is available, time-of-flight calculation can add more information on the likely position of the event along the line.

Limitations in the timing resolution of the scanner will determine the accuracy of the positioning along this line. Further, limitations in the determination of the location of the original scintillation events will determine the ultimate spatial resolution of the scanner. Also, the specific characteristics of the isotope (i.e., energy of the positron) will also contribute, via positron range and co-linearity of the two gamma rays, to the determination of the spatial resolution of the specific agent.

The above process needs to be repeated for a large number of events. While every case needs to be analyzed to determine how many counts (paired events) are required to support the imaging tasks, current practice dictates that a typical 100 cm long, FDG (fluoro-deoxyglucose) study should accumulate a few 100 millions counts. The time it takes to accumulate this number of counts is determined by the injected dose and the sensitivity and counting capacity of the scanner.

The PET scanner is typically substantially cylindrical to be able to capture as much as possible of the radiation which should be, by definition, isotropic. Since the opposite detection of two gamma rays is necessary to create an event, the sensitivity is approximately the square of the solid angle created by the detector arrangement. For example, the use of a partial ring and rotation to capture the missing angles is possible, but has severe consequences regarding the overall sensitivity. From the cylindrical geometry, in which all gamma rays included in a plane would have a chance to interact with the detector, an increase of the axial dimension would have a very beneficial effect on the sensitivity or ability to capture the radiation, leading to the ultimate design of a sphere, in which all gamma rays would have the opportunity to be detected. However, the spherical design is not feasible due to the large size and high costs required for creating a spherical PET scanner suitable for application on humans. Therefore, the modern PET scanner includes a cylindrical geometry with the axial extent as a variable.

Once the overall geometry of the scanner is determined, the next challenge is to dispose as much scintillating material as possible in the gamma ray path to stop and convert as many gamma rays as possible into light. Two directions of optimization are considered in this process. First, the "in-plane" sensitivity necessitates that as much crystal as possible (i.e., crystal thickness) be disposed within a PET detector. Second, for a given crystal thickness, the axial length of the detector-cylinder defines the overall system sensitivity, which is approximately proportional to the square of the axial length (the solid angle subtended by a point in the middle of a cylinder). Additionally, practical cost considerations are unavoidably part of the optimization process.

While it is generally desirable to obtain as large of an axial length as possible for sensitivity, clinical needs may impose an additional set of constraints. For example, some clinical tests may require a PET scanner to cover an entire organ such as the lung or multiple organs such as the heart and carotids. Therefore, the goal of designing a PET scanner is to optimize the cost, sensitivity, and axial length of the PET scanner.

BRIEF DESCRIPTION OF THE DRAWINGS

A more complete appreciation of the present advancements and many of the attendant advantages thereof will be readily obtained as the same becomes better understood by reference to the following detailed description when considered in connection with the accompanying drawings, wherein.

DETAILED DESCRIPTION

Figure 1A:
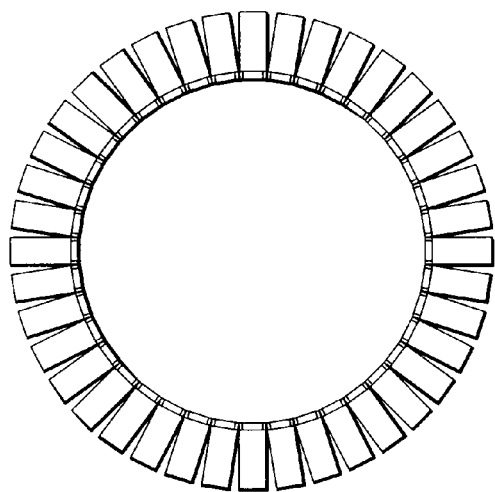
FIG. 1A illustrates a PET scanner configuration with all of the modules arranged in a full cylinder.

According to some embodiments, a gamma ray detection system includes a plurality of detector modules having a same length, each detector module being configured to detect gamma rays generated from positron annihilation events. A first detector module of the plurality of detector modules is shifted by a predetermined distance in an axial direction from a second detector module of the plurality of detector modules that is adjacent to the first detector module, where the predetermined distance is less than the length of the detector modules.

According to some embodiments, a PET system includes a plurality of radiation detector modules having a same length and arranged in a cylindrical ring, each detector module being configured to detect gamma rays generated from positron annihilation events. A first detector module of the plurality of detector modules is shifted by a predetermined distance in an axial direction from a second detector module of the plurality of detector modules that is adjacent to the first detector module, where the predetermined distance is less than the length of the detector modules. The first and second detector modules form a central scanning region having an axial field of view equal to the length of the detector modules minus the predetermined distance. The first and second detector modules further form a first peripheral scanning region having an axial field of view equal to the predetermined distance. The first and second detector modules also form a second peripheral scanning region having an axial field of view equal to the predetermined distance.

According to some embodiments, a non-transitory computer readable storage medium storing a program, which when executed by a computer, causes the computer to collect, from a plurality of detector modules, event data corresponding to annihilation events. The plurality of detector modules each have a same length and are arranged in a cylindrical ring, where each detector module is configured to detect gamma rays generated from the annihilation events. A first detector module of the plurality of detector modules is shifted by a predetermined distance in an axial direction from a second detector module of the plurality of detector modules that is adjacent to the first detector module, where the predetermined distance is less than the length of the detector module.

According to one embodiment, a PET scanner includes PET detector modules arranged within a cylindrical ring or polygonal shape with every other detector module shifted by a predetermined distance. By shifting every other detector module of the PET scanner along the axis of the cylinder, the axial field of view (FOV) is increased while the cost and overall sensitivity of the PET scanner remains the same.

According to some embodiments, the sensitivity of a PET scanner refers to the probability of a PET scanner to capture an annihilation event. Further, according to some embodiments, the axial FOV of a PET scanner refers to the area of the PET scanner that can capture an annihilation event. In additional embodiments, an axial length includes the length of an object perpendicular to an opening of a PET scanner. For example, when a patient is inserted into a PET scanner, an axial length is along the axis in which the patient is inserted into the PET scanner.

In some embodiments disclosed herein, PET scanners are composed of several thousand individual crystals, arranged in modules defining a complete cylinder or multi-facetted polygons. Crystal elements generally have a cross-section of roughly 4 mm×4 mm. However, smaller dimensions and a non-square cross-section are also possible. The length (i.e., depth) of the crystal determines how likely a gamma ray is captured. Crystals may be arranged in a plurality of detector modules, which are the main building blocks of the PET scanner. The length of the crystal elements within the detector module may range from 10 to 30 mm.

When designing a PET scanner, it is desirable to minimize the costs of a PET scanner while increasing the PET scanner's FOV. In the following comparison of PET scanners, the crystal depth, total amount of crystal (i.e., scintillation material), and detector diameter are fixed (i.e., based on these dimensions, each PET scanner has the same cost).

Figure 1B:
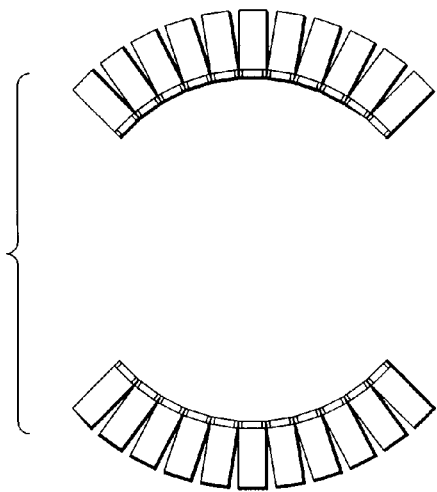
FIG. 1B illustrates another PET scanner configuration with all of the detector modules arranged in two partial arcs.

FIG. 1A illustrates a PET scanner configuration with all of the modules arranged in a full cylinder. FIG. 1B illustrates another PET scanner configuration with all of the detector modules arranged in two partial arcs. As indicated above, the partial arc PET scanner (FIG. 1B) has the same amount of scintillation material as the full cylinder PET scanner (FIG. 1A), but with a larger axial length z.

The sensitivity of a PET scanner is proportional to the in-plane solid angle $\Omega$ multiplied by the axial length z. Therefore, the sensitivity of the full cylinder PET scanner is approximately $(\Omega \cdot z)^2$. The sensitivity of the partial arc PET scanner is $(\Omega/2 \cdot 2z)^2$. Accordingly, the full cylinder and partial arc cylinder have approximately the same sensitivity.

While the cost and sensitivity of the full cylinder and partial arc configurations are approximately the same, the sampling properties of the two PET scanners are quite different. For example, rotation of the partial arc PET scanner is necessary to cover all angles. Further, it is impossible to properly sample any dynamic processes with the partial arc geometry due to the time it takes to rotate the detector modules to cover the missing angles.

Figure 1C:
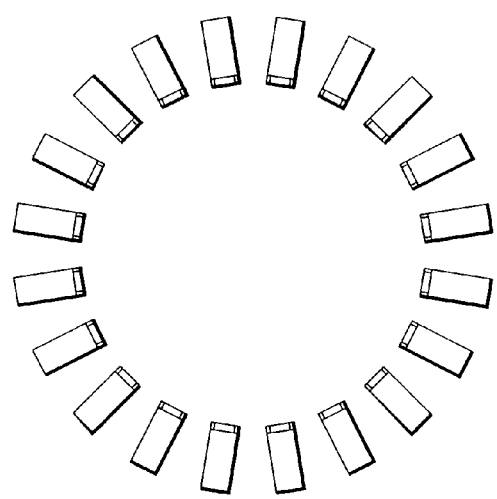
FIG. 1C illustrates a PET scanner configuration in which the detector modules are distributed evenly in a cylindrical ring.

FIG. 1C illustrates a PET scanner configuration in which the detector modules are distributed evenly in a cylindrical ring. However, in this configuration, to approximately match the sensitivity of this PET scanner with the full cylinder and the partial arc PET scanners, scintillation material is moved to increase the length of the detector modules, which creates the gaps illustrated in FIG. 1C. Compared to the partial arc PET scanner, the cylindrical PET scanner illustrated in FIG. 1C allows for a smaller rotation to be performed to obtain the missing angles. However, even with the reduced gap compared to the partial arc design the presence of the gap may prevent accurate sampling for dynamic processes.

Figure 1D:
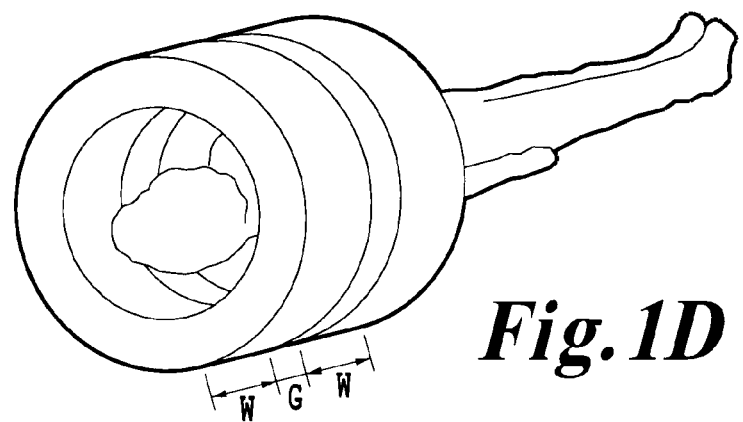
FIG. 1D illustrates a PET scanner configuration having two rings with the same amount of scintillation material as the full cylinder and partial arc scanners.

FIG. 1D illustrates a PET scanner configuration having two rings with the same amount of scintillation material as the full cylinder and partial arc scanners. Accordingly, the two-ring PET scanner has approximately the same sensitivity as the full cylinder with an axial FOV of 2 W. While there is a gap G in the two-ring PET scanner illustrated in FIG. 1D, time of flight (TOF) reconstruction helps complete the gap area G producing an "adequate" spatio-temporal sampling.

The PET scanners illustrated in FIGS. 1A-1D offer only the option of linearly increasing the cost of the scanner to increase the axial FOV of the scanner to capture a larger dynamic image of the patient. The circumferentially distributed detector material with at least one gap (FIGS. 1B-1C) is intrinsically poor in producing an adequate sampling, and would perform poorly in capturing a full dynamic process. The axially distributed material (FIG. 1D) combined with time-of-flight reconstruction may offer a better compromise compared to the other scanners, but the quality of the reconstructed image in the gap would depend on the quality of the time of flight information, and the system would always offer poorer performance in the middle of the axial FOV where, in practice, the area or organ of interest may be placed.

Figure 2:
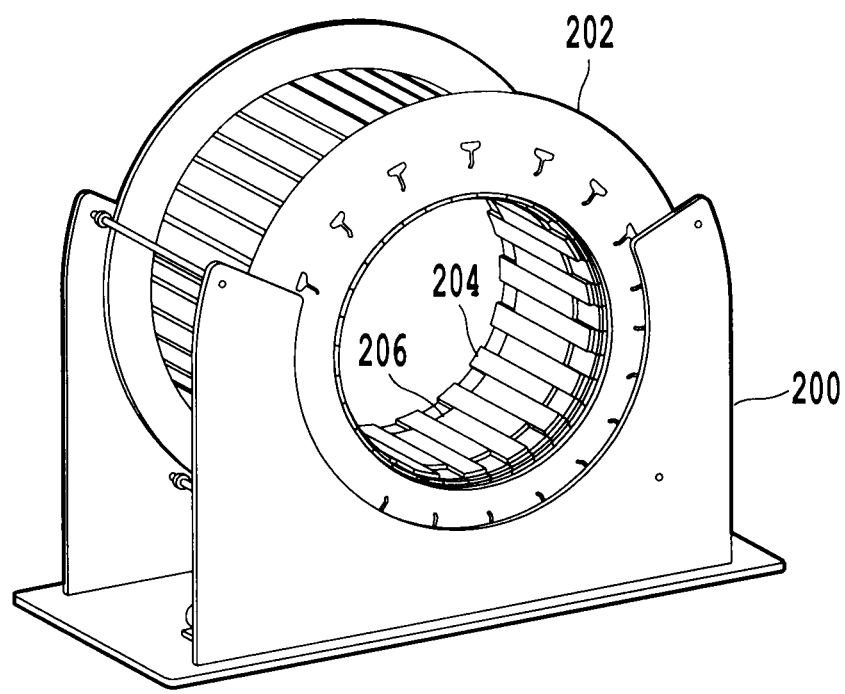
FIG. 2 illustrates a cylindrical PET scanner with shifted detector modules.

FIG. 2 illustrates an example cylindrical PET scanner 200 having a cylindrical detector ring 202. According to some embodiments, the PET detector includes a plurality of detector modules 204 having a length W. As illustrated in FIG. 2, every other detector module is shifted axially by a distance d, where d is less than W. The patient or subject to be imaged is placed inside the cylinder 202. As illustrated in FIG. 2, a gap 206 is created by shifting the detector module 204. However, according to some embodiments, the width of the gap 206 is the same as the width of the detector module 204. Accordingly, rotating the PET detector ring 202 an amount equivalent to the width of the detector module 204 provides complete sampling since each gap between each pair of detector modules is covered.

In some embodiments, the PET detector ring 202 is rotatable. As an example, the PET detector ring 202 may be attached to a motor that is configured to rotate the PET detector ring 202 by a predetermined amount. In further embodiments, the PET detector ring 202 includes a sensor that monitors the rotation of the PET detector ring 202. In some embodiments, a sensor is positioned at any desirable location on the perimeter of the PET detector ring 202 to determine and store an angle of rotation of the detector modules 204. As an example, the sensor monitors how many radians that the PET detector ring 202 has rotated at a particular time, which is used in image reconstruction. In other embodiments, a sensor is positioned at a motor that rotates the PET detector ring 202, where a number of rotations of the motor is measured and correlated with the angle of rotation of the detector modules.

According to some embodiments, the PET scanner 200 has the same amount of scintillation material as the PET scanners illustrated in FIGS. 1A-1D. Accordingly, the PET scanner 200 has approximately the same cost and sensitivity as the PET scanners illustrated in FIGS. 1A-1C. However, by shifting the detector modules 204 as illustrated in FIG. 2, the axial FOV of the PET scanner 200 is increased compared to PET scanners illustrated in FIGS. 1A-1C. In this regard, the axial FOV of the PET scanner 200 is approximately W+d, whereas the axial FOV of the unshifted scanner illustrated in FIG. 1A is W, 2 W for the scanners of FIGS. 1B and 1C, respectively, and W+G for the scanner of FIG. 1D.

Figure 3A:
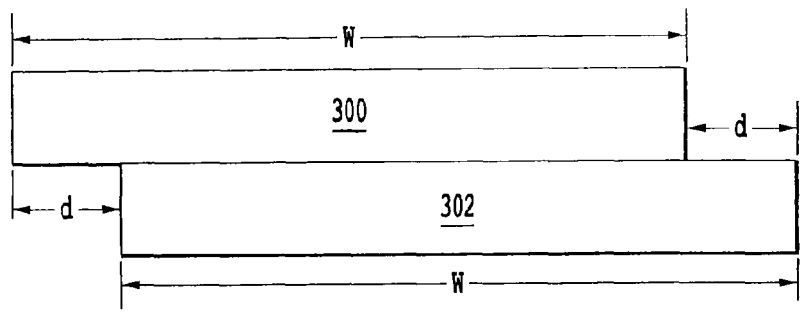
FIG. 3A illustrates a pair of detector modules.

FIG. 3A illustrates a pair of detector modules 300 and 302. In one embodiment, the pair of detector modules 300 and 302 correspond to a pair of detector modules 204 located in the PET detector ring 202 (FIG. 2). According to some embodiments, the pair of detector modules 300 and 302 each has a length W, the same width, and are shifted by an amount d. When the PET scanner 200 includes the same amount of scintillation material as the PET scanners illustrated in FIGS. 1A-1D, the overall sensitivity of each of the PET scanners is approximately the same. However, the PET scanner 200 including the pair of shifted detector modules 300 and 302 includes three separate scanning regions that increase the axial FOV of the PET scanner compared to the PET scanners illustrated in FIGS. 1A-1D. In this regard, the shifted pair of detector modules 300 and 302 include, in some embodiments, a central scanning region, a first peripheral scanning region, and a second peripheral scanning region.

Figure 3B:
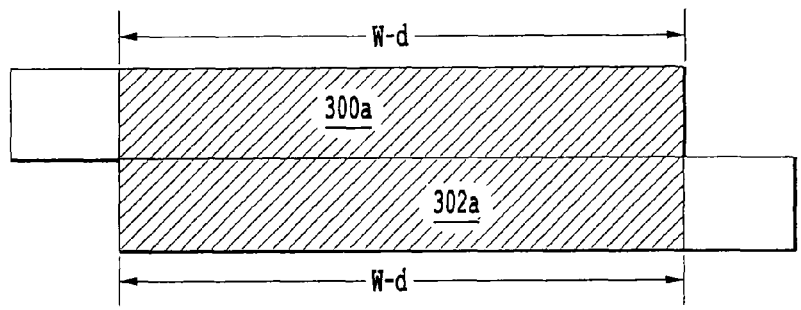
FIG. 3B illustrates, in one embodiment, a central scanning region.

FIG. 3B illustrates, in one embodiment, a central scanning region including areas 300a and 302a of detector modules 300 and 302, respectively. The dimensions of the areas 300a and 300b correspond to 2 times (W−d) times the width of detector module 300. The central scanning region offers a complete sampling of any annihilation event falling within the area corresponding to the central scanning region. For example, since there is no gap between a pair of detector modules in the area corresponding to the central scanning region, each annihilation event falling in this area is captured, which offers the best possible description of any dynamic process.

Figure 3C:
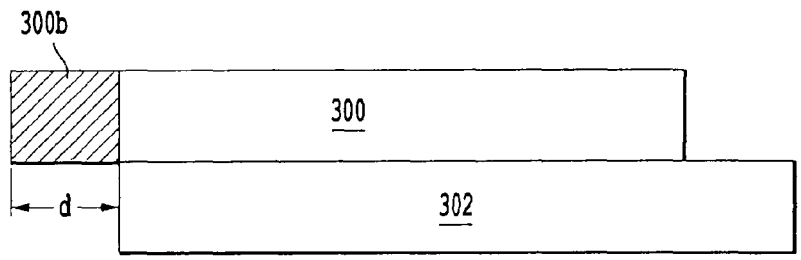
FIG. 3C illustrates, in one embodiment, a peripheral scanning region.
Figure 3D:
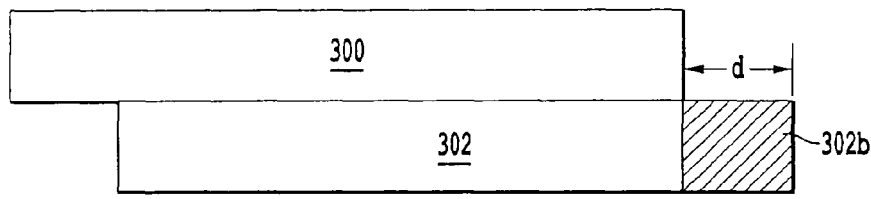
FIG. 3D illustrates another peripheral scanning region.

FIG. 3C illustrates, in one embodiment, a peripheral scanning region including area 300b of detector module 300. The area 300b is d times the width of detector module 300. FIG. 3D illustrates another peripheral scanning region including area 302b of detector module 302. The area 302b is d times the width of detector module 302. The peripheral scanning regions offer partial sampling with ¼ of the sensitivity of the central scanning region. However, since the areas 300b and 302b corresponding to the peripheral scanning regions extend beyond the areas 300a and 302a corresponding to the central scanning region, the peripheral scanning regions extend the axial FOV of the PET scanner 200 by a distance d, at ¼ of the sensitivity compared to the unshifted PET scanners illustrated in FIGS. 1A-1D.

Using the three scanning regions (FIGS. 3B-3D) included in the shifted pair of detector modules, a pair of events occurring within the peripheral scanning regions or central scanning regions of any detector module included in the PET detector ring 202 are combined, according to some embodiments, to form a hybrid detection of events.

Figure 4:
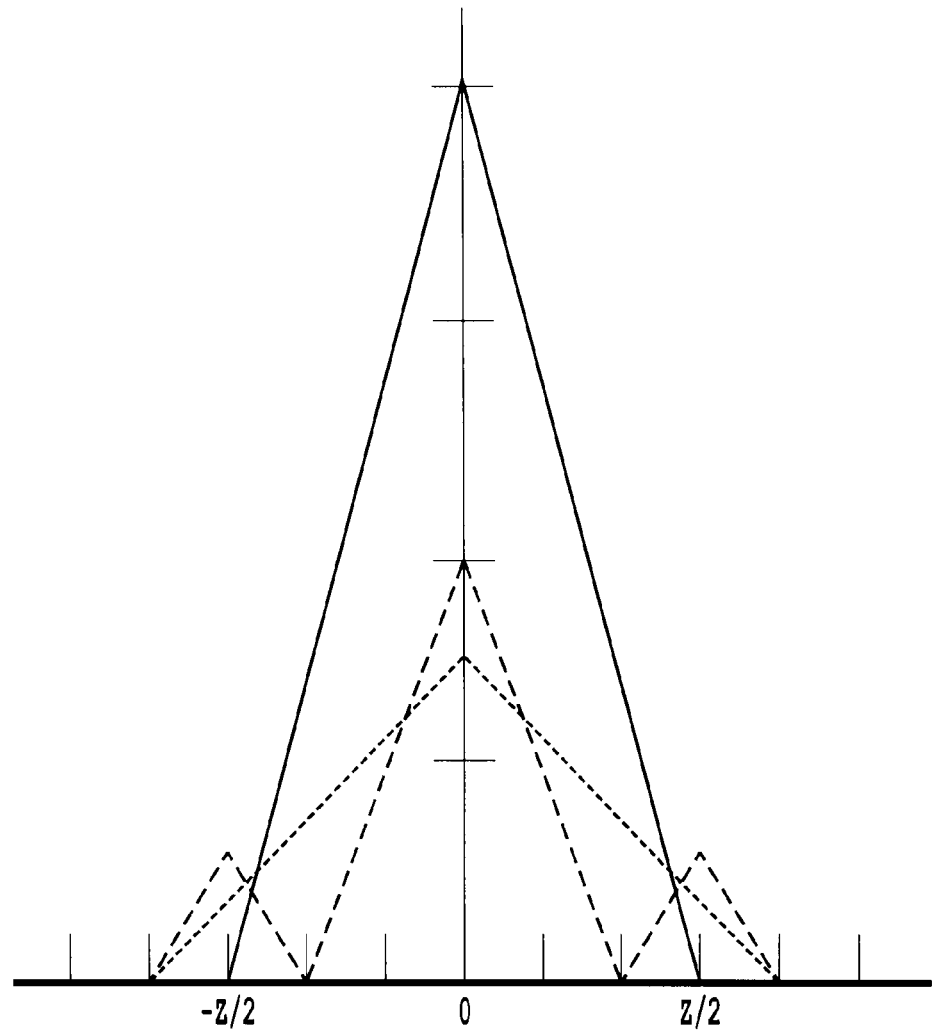
FIG. 4 illustrates a graph showing how sensitivity is changing across the axial FOV.

FIG. 4 is a graph showing how sensitivity changes across the axial FOV. The horizontal axis represents the axial length (Z) of a cylindrical PET detector ring, and the vertical axis represents relative sensitivity.

The full cylindrical scanner (FIG. 1A) has an axial sensitivity profile as represented by the solid line with the area under the curve proportional to the overall sensitivity. The axial sensitivity profile of the PET scanner including the shifted detector modules (FIG. 2) is composed of the three dashed portions including the central portion corresponding to the central scanning region, and the two lateral regions corresponding to the peripheral scanning regions. The height of the central portion is proportional to the amount of shift between a pair of detector modules. The axial sensitivity profile corresponding to mixed region events is composed of the dotted line. The overall system sensitivity is the addition of all dashed and dotted regions so that the total surface is substantially equivalent to the original solid line triangle. Thus, the shifted PET scanner and the unshifted PET scanner have approximately the same system sensitivity.

The presence of the "dotted line" region of mixed events is more than just adding counts. Without mixing events, the shifted scanner would need to rotate to complete an adequate sampling of the object beyond the original −Z/2 to +Z/2 area. The mixed event area includes sampling lines not available in either of the lateral regions. Therefore, the mixed event area helps the overall image quality of the reconstruction of captured samples. Further, in addition to creating new lines of response not available in the "sub-scanners" taken individually, ToF reconstruction would further utilize these events to improve the reconstruction quality of an image, since more samples are available for reconstruction.

Figure 5A:
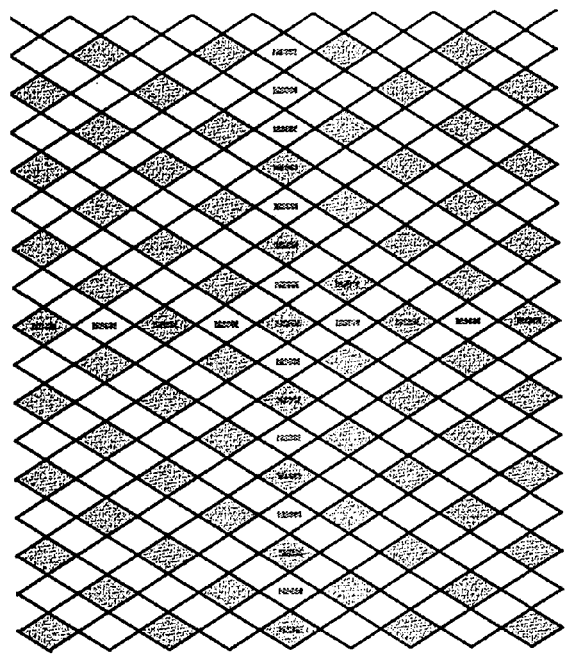
FIG. 5A illustrates an example Radon space.
Figure 5B:
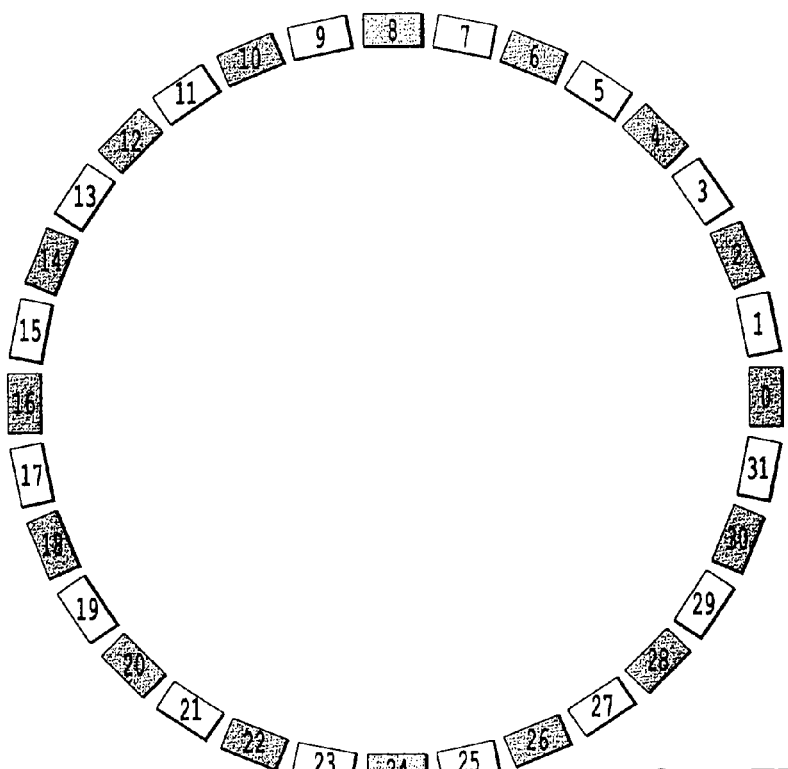
FIG. 5B illustrates an example detector ring.

FIG. 5A illustrates an example Radon space. In a Radon representation, each line connecting a detector element to another (e.g., the center of module 8 to the center of module 24 in FIG. 5B) has an angle and a distance from the axis (e.g., the angle is 90 degrees or vertical, and the distance is 0 cm when the center of module 8 is connected to the center of module 24). A point is added to the graph of 5A to represent the line, where the vertical axis represents the angle, and the horizontal axis represents the distance. As illustrated in FIG. 5B, the range of angle and distance supported by the limited size of modules 8 and 24 defines a parallelogram in FIG. 5A. All cells are available in a completely sampled case, and gantry rotation, equivalent to a up-down movement of the entire Radon graph would eventually cover all cells.

The "mixed" events are equivalent to connecting one cell in the partial sampled Radon graph to any cell on the complete case. The more the plane of consideration moves axially toward the complete region, the more each of the cell "grows" as a weighted average between the two regions. As understood by one ordinary skill in the art, the Radon graph illustrated in FIG. 5A is for illustrative purposes, where an exact profile would include more details. One of ordinary skill in the art can see that a line connecting any two modules in FIG. 5B has an endpoint "a" and another endpoint "b." In the area of the detector modules providing complete sampling (e.g., central scanning regions 300a and 302a in FIG. 3B), any endpoint "a" can be connected to any other end point "b." In the peripheral regions (e.g. peripheral scanning regions 300b and 302b in FIGS. 3C and 3D, respectively) one-half of each endpoint "a" falling in the peripheral region can be connected to one-half of the endpoints "b" falling in the peripheral region, which provides ¼ sensitivity compared to both end points falling in the central scanning region. Further, ½ of the possible endpoints "a" falling in the peripheral scanning region can be connected with any endpoint "b" falling in the central scanning region, which provides ½ sensitivity compared to both end points falling in the central scanning region. Accordingly, the overall useful axial FOV of the shifted scanner is larger than the un-shifted scanner with the same amount of scintillator material and a substantially similar overall system sensitivity. Further, with one detector width of rotation, complete sampling can be obtained. Therefore, the PET scanner with shifted detector modules is more suitable for sampling dynamic processes.

In addition, if multiple axial steps are required to cover the entire region of interest (whole-body imaging, for instance), complete sampling can be obtained by moving the gantry axially by a full z. This would result in the gaps on one partially sampled area to be filled by the opposite end, which has, by definition, a complementary pattern.

Figure 6:
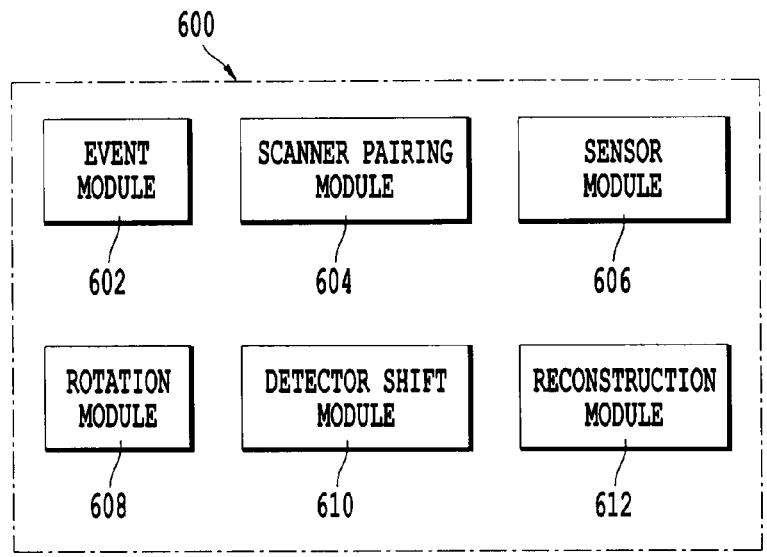
FIG. 6 illustrates an example PET detector system including one or more modules.

FIG. 6 illustrates an example PET detector system 600 including one or more modules. Modules of the PET detector system 600 are hardware or a hardware/software combination. In some embodiments, the PET detector system 600 is implemented by a program or programs that are executed on a CPU. However, the modules can be implemented as special-purpose hardware circuits. According to one embodiment, the PET detector system 600 includes an event module 602, a scanner pairing module 604, a sensor module 606, a rotation module 608, a detector shift module 610, and a reconstruction module 612.

According to one embodiment, the event module records and keeps track of annihilation events captured by each detector module included in a PET detector ring. For example, referring to FIG. 2, when a patient after being injected, inhaling, or ingesting a pharmaceutical agent is placed in the PET detector ring 202, the event module 602 records and keeps track of all annihilation events captured by each of the detector modules 604 included in the PET detector ring 202. In one embodiment, the scanner pairing module 604 pairs an event from a detection module with an event from another detection module.

According to one embodiment, the sensor module 606 is in communication with a sensor (not shown) that keeps track of an angle corresponding to the rotation of a PET detector ring. In one embodiment, the rotation module 608 instructs a motor to rotate the PET detector ring. As an example, the rotation module 608 instructs a motor to rotate the PET detector ring 202 a predetermined multiple of the width of each detector module 204. In further embodiments, the sensor module 606 keeps track of the amount of rotation of the PET detector ring 202 as a function of time, which is used for image reconstruction.

According to one embodiment, the detector shift module 610 changes the amount of shift between each detector module on a case by case basis to accommodate various organ or patient sizes. As an example, the detector shift module 610 can change the amount of shift between each detector module 204 (FIG. 2). By increasing the shift between detector modules, the axial FOV can be increased. In one embodiment, the reconstruction module 612 uses any desired methodology to reconstruct an image using information from the event module 602, scanner pairing module 604, sensor module 606, and rotation module 608. For example, list mode reconstruction can be performed, as set forth in related application Ser. No. 12/571,562, the contents of which are incorporated herein by reference.

Figure 7:
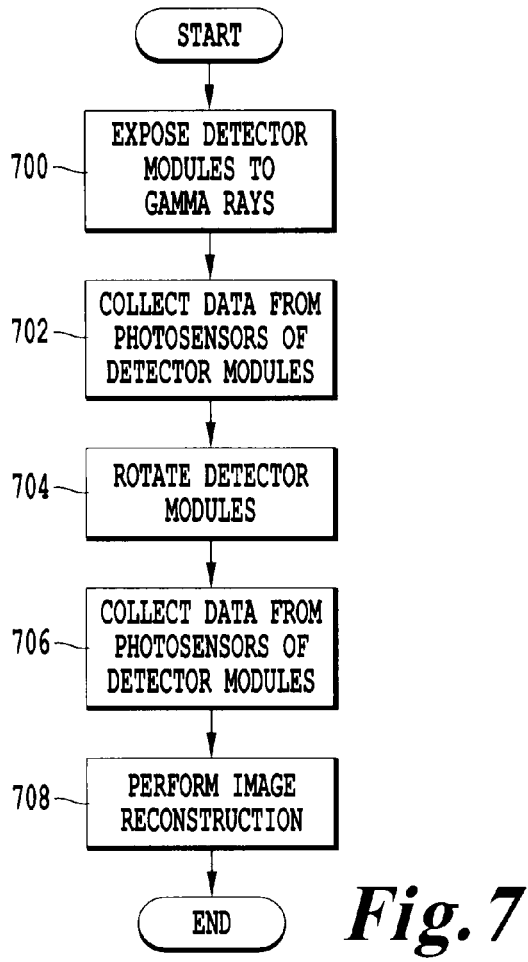
FIG. 7 illustrates an example process for capturing annihilation events using shifted detector modules.

FIG. 7 illustrates an example process for capturing annihilation events using shifted detector modules. In one embodiment, the process illustrated in FIG. 7 starting at step 702 is performed by a CPU.

The process starts at step 700 by exposing detector modules to gamma rays. As an example, referring to FIG. 2, when a patient, after ingesting a radial pharmaceutical agent, is placed in the PET detector ring 202, the detector modules 204 are radiated with 511 KeV gamma rays corresponding to annihilation events.

The process proceeds to step 702 to collect data from photosensors of detector modules. As an example, the event module 602 records and keeps track of each detector module 204 included in detector ring 202 that has captured an annihilation event.

The process proceeds to step 704 to rotate the detector modules. As an example, the rotation module 606 rotates the PET detector ring 202 by a predetermined amount, where the sensor module 606 keeps track of the angle of rotation of the detection ring 202. In some embodiments, a PET detector ring 202 is rotated after a predetermined period of time has passed after the first annihilation event is captured. In alternative embodiments, the rotation is continuous, where information on the angle of rotation is available for each event and sent to a processor to perform list mode reconstruction.

The process proceeds to step 706 to collect data from the photosensors of the detection modules, as functionally described above, after rotation of the PET detector ring 202. The process then proceeds to step 708 to perform image reconstruction. As an example, the reconstruction module 612 uses any desired methodology to perform image reconstruction using information from the event module 602, the scanner pairing module 604, the sensor module 606, and the rotation module 608. According to embodiments, rotation information is used for all events detected in the peripheral and center regions to reconstruct an image.

According to some embodiments, iterative reconstruction is used to reconstruct an image. Iterative reconstruction uses a detailed description of the scanner geometry and allows for complex cases (e.g., mixed events) to be used. Compared to other scanners using the same amount of scintillation material as the shifted scanner, and therefore costing the same, the shifted scanner is clinically more useful by capturing a larger FOV.

Figure 8:
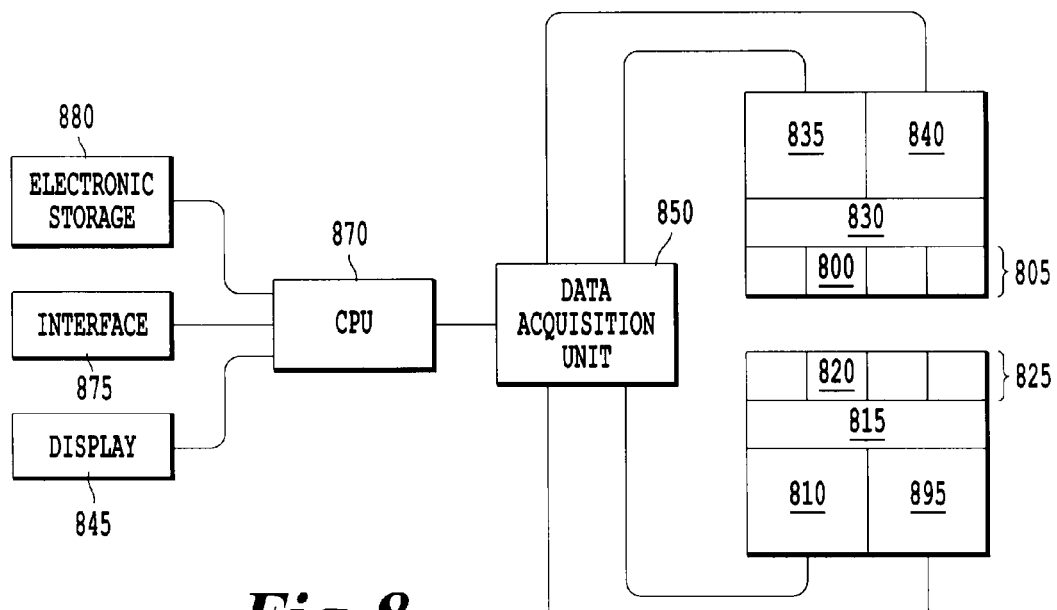
FIG. 8 is a block diagram of an example data acquisition system.

FIG. 8 is a schematic drawing of a gamma ray detection system that can be used to obtain gamma ray or PET event information according to embodiments of the present advancements. In FIG. 8, photomultiplier tubes 835 and 840 are arranged over light guide 830, and the array of scintillation crystals 805 is arranged beneath the light guide 830. A second array of scintillation crystals 825 is disposed opposite the scintillation crystals 805 with light guide 815 and photomultiplier tubes 895 and 810 arranged thereover. The photomultiplier tubes, light guide, and scintillation crystals can form a detector module, wherein the gamma ray detection system includes a plurality of detector modules arranged in a ring.

In FIG. 8, when gamma rays are emitted from a body under test (not shown), the gamma rays travel in opposite directions, approximately 180° from each other. Gamma ray detection occurs simultaneously at scintillation crystals 800 and 820, and a scintillation event is determined when the gamma rays are detected at scintillation crystals 800 and 820 within a predefined time limit. Thus, the gamma ray timing detection system detects gamma rays simultaneously at scintillation crystals 800 and 820. However, for simplicity only, gamma ray detection is described relative to scintillation crystal 800. One of ordinary skill in the art will recognize, however, that the description given herein with respect to scintillation crystal 800 is equally applicable to gamma ray detection at scintillation crystal 820.

Each photomultiplier tube 810, 835, 840 and 895 is respectively connected to data acquisition unit 850. Data acquisition unit includes hardware configured to process the signals from the photomultiplier tubes. The data acquisition unit 850 measures the arrival time of the gamma ray. The data acquisition unit 850 produces two outputs (one for the combination of PMT 835/840 and one for the combination of PMT 810/895) which encodes the time of the discriminator pulse relative to a system clock (not shown). For a time-of-flight PET system, the data acquisition unit 850 typically produces a time stamp with an accuracy of 15 to 25 ps. The data acquisition unit measures the amplitude of the signal on each PMT (four of the outputs from data acquisition unit 850).

The data acquisition unit outputs are provided to a CPU 870 for processing. The processing consists of estimating an energy and position from the data acquisition unit outputs and an arrival time from the time stamps output for each event, and may include the application of a many correction steps, based on prior calibrations, to improve the accuracy of the energy, position, and time estimates.

According to embodiments, the CPU 870 is configured to implement one or more of the modules illustrated in FIG. 6. In further embodiments, the CPU 870 is configured to implement the process illustrated in FIG. 7. As one of ordinary skill in the art would recognize, the CPU 870 can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog or any other hardware description language and the code may be stored in an electronic memory directly within the FPGA or CPLD, or as a separate electronic memory. Further, the electronic memory may be non-volatile, such as ROM, EPROM, EEPROM or FLASH memory. The electronic memory may also be volatile, such as static or dynamic RAM, and a processor, such as a microcontroller or microprocessor, may be provided to manage the electronic memory as well as the interaction between the FPGA or CPLD and the electronic memory.

Alternatively, the CPU 870 may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xeon processor from Intel of America or an Opteron processor from AMD of America and an operating system, such as Microsoft VISTA, UNIX, Solaris, LINUX, Apple, MAC-OS and other operating systems known to those skilled in the art.

Once processed by the CPU 870, the processed signals are stored in electronic storage 880, and/or displayed on display 845. As one of ordinary skill in the art would recognize, electronic storage 880 may be a hard disk drive, CD-ROM drive, DVD drive, FLASH drive, RAM, ROM or any other electronic storage known in the art. Display 845 may be implemented as an LCD display, CRT display, plasma display, OLED, LED or any other display known in the art. As such, the descriptions of the electronic storage 880 and the display 845 provided herein are merely exemplary and in no way limit the scope of the present advancements.

FIG. 8 also includes an interface 875 through which the gamma ray detection system interfaces with other external devices and/or a user. For example, interface 875 may be a USB interface, PCMCIA interface, Ethernet interface or any other interface known in the art. Interface 875 may also be wired or wireless and may include a keyboard and/or mouse or other human interface devices known in the art for interacting with a user.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A gamma ray detection system, comprising:
a plurality of detector modules having a same length, each detector module being configured to detect gamma rays generated from positron annihilation events,
wherein a first detector module of the plurality of detector modules is shifted by a predetermined distance in an axial direction from a second detector module of the plurality of detector modules that is adjacent to the first detector module to generate a shifted detector having a central scanning region, a first peripheral scanning region, and a second peripheral scanning region so that the effective overall axial field of view of the shifted detector that is useable for imaging is larger than an axial field of view of the detector modules when arranged unshifted, the predetermined distance being less than the length of the detector modules.

2. The gamma ray detection system according to claim 1, wherein every other detector module included in the plurality of detector modules is shifted by the predetermined distance in the axial direction.

3. The gamma ray detection system according to claim 1, further comprising:
a processor configured to collect and process event data obtained from each detector module of the plurality of detector modules; and
a motor to rotate the plurality of detector modules by a predetermined multiple of a width of each detector module in response to a command received from the processor.

4. The gamma ray detection system according to claim 3, further comprising:

a sensing unit configured to detect and store an angle of rotation associated with the plurality of detector modules as a function of time, wherein the processor is configured to reconstruct an image using the collected event data and the detected angle of rotation.

5. The gamma ray detection system of claim 1, further comprising:

a detector shift controller configured to change the predetermined distance by which the first detector module is shifted from the second detector module based on a region of interest to be imaged.

6. The gamma ray detection system of claim 1, wherein the central scanning region of the shifted detector includes same-sized portions of both the first and second detector modules.

7. A Positron Emission Tomography (PET) system, comprising:

a plurality of radiation detector modules having a same length and arranged in a cylindrical ring, each detector module being configured to detect gamma rays generated from positron annihilation events, wherein a first detector module of the plurality of detector modules is shifted by a predetermined distance in an axial direction from a second detector module of the plurality of detector modules that is adjacent to the first detector module to generate a shifted detector having a central scanning region, a first peripheral scanning region, and a second peripheral scanning region so that the effective overall axial field of view of the shifted detector that is useable for imaging is larger than an axial field of view of the detector modules when arranged unshifted, the predetermined distance being less than the length of the detector modules, wherein the central scanning region has an axial field of view equal to the length of the detector modules minus the predetermined distance, the first peripheral scanning region has an axial field of view equal to the predetermined distance, and the second peripheral scanning region has an axial field of view equal to the predetermined distance.

8. The PET system according to claim 7, further comprising:

a processor configured to collect and process event data and to combine an annihilation event corresponding to the central scanning region with an annihilation event corresponding to the first peripheral scanning region.

9. The PET system according to claim 7, further comprising:

a processor configured to collect and process event data and to combine an annihilation event corresponding to the central scanning region with an annihilation event corresponding to the second peripheral scanning region.

10. The PET system according to claim 9, further comprising:

a processor configured to collect and process event data and to combine an annihilation event corresponding to the first peripheral scanning region with an annihilation event corresponding to the second peripheral scanning region.

11. The PET system according to claim 7, wherein every other detector module included in the plurality of detector modules is shifted by the predetermined distance in the axial direction.

12. The PET system according to claim 11, further comprising:

a sensing unit configured to detect and store an angle of rotation associated with the plurality of detector modules as a function of time, wherein the processor is configured to reconstruct an image using the collected event data and the detected angle of rotation.

13. The PET system according to claim 7, further comprising:

a processor configured to collect and process event data; and a motor to receive a command from the processor to rotate the cylindrical ring including the plurality of detectors by a predetermined multiple of a width of the first detector module so that event data corresponding to the first peripheral scanning region complements event data corresponding to the second peripheral scanning region.

14. A non-transitory computer readable storage medium storing a computer program, which when executed by a computer, causes the computer to:

collect, from a plurality of detector modules, event data corresponding to annihilation events, the plurality of detector modules having a same length and arranged in a cylindrical ring, each detector module being configured to detect gamma rays generated from the annihilation events, wherein a first detector module of the plurality of detector modules is shifted by a predetermined distance in an axial direction from a second detector module of the plurality of detector modules that is adjacent to the first detector module to generate a shifted detector having a central scanning region, a first peripheral scanning region, and a second peripheral scanning region so that the effective overall axial field of view of the shifted detector that is useable for imaging is larger than an axial field of view of the detector modules when arranged unshifted, the predetermined distance being less than the length of the detector module.

15. The non-transitory computer readable storage medium according to claim 14, wherein the computer program further causes the computer to:

combine an annihilation event corresponding to a central scanning region with an annihilation event corresponding to a peripheral scanning region, wherein the central scanning region includes an axial field of view equal to the length of the detector modules minus the predetermined distance, and the peripheral scanning region includes an axial field of view equal to the predetermined distance.

16. The non-transitory computer readable storage medium according to claim 14, wherein the computer program further causes the computer to:

combine an annihilation event corresponding to a first peripheral scanning region with an annihilation event corresponding to a second peripheral scanning region, wherein the first and second peripheral scanning regions each include an axial field of view equal to the predetermined distance.

17. The non-transitory computer readable storage medium according to claim 16, wherein the computer program further causes the computer to:

instruct a motor to rotate the cylindrical ring including the plurality of detectors by a predetermined multiple of a width of the first detector module so that event data corresponding to the first peripheral scanning region complements event data corresponding to the second peripheral scanning region; and reconstruct an image using the data collected from the plurality of detector modules.

* * * * *